(12) United States Patent
Balboni

(10) Patent No.: US 10,295,413 B2
(45) Date of Patent: May 21, 2019

(54) FEVER ALERT SYSTEM

(71) Applicant: Ann Balboni, Bronxville, NY (US)

(72) Inventor: Ann Balboni, Bronxville, NY (US)

(*) Notice: Subject to any disclaimer, the term of this patent is extended or adjusted under 35 U.S.C. 154(b) by 40 days.

(21) Appl. No.: 15/724,607

(22) Filed: Oct. 4, 2017

(65) Prior Publication Data

US 2018/0055457 A1 Mar. 1, 2018

Related U.S. Application Data

(63) Continuation-in-part of application No. 14/243,422, filed on Apr. 2, 2014, now Pat. No. 9,835,496.

(60) Provisional application No. 61/809,509, filed on Apr. 8, 2013.

(51) Int. Cl.

| | |
|---|---|
| *G01K 1/00* | (2006.01) |
| *G01K 1/02* | (2006.01) |
| *A61B 5/00* | (2006.01) |
| *A61B 5/01* | (2006.01) |
| *A44C 5/00* | (2006.01) |
| *G01K 13/00* | (2006.01) |
| *A61B 90/30* | (2016.01) |

(52) U.S. Cl.
CPC ............ *G01K 1/024* (2013.01); *A44C 5/0015* (2013.01); *A61B 5/0008* (2013.01); *A61B 5/01* (2013.01); *A61B 5/6817* (2013.01); *A61B 5/7282* (2013.01); *A61B 5/746* (2013.01); *A61B 5/7445* (2013.01); *A61B 5/7455* (2013.01); *G01K 13/002* (2013.01); *A61B 2090/304* (2016.02); *A61B 2090/309* (2016.02)

(58) Field of Classification Search
CPC ..................................................... G01K 1/024
See application file for complete search history.

(56) References Cited

U.S. PATENT DOCUMENTS

| 8,107,920 B2 | 1/2012 | Ben Ayed |
| 2001/0044588 A1 | 11/2001 | Mault |
| 2005/0245839 A1 | 11/2005 | Stivoric et al. |
| 2006/0078037 A1 | 4/2006 | Lee et al. |
| 2007/0041424 A1 | 2/2007 | Lev et al. |

(Continued)

FOREIGN PATENT DOCUMENTS

WO 2014168891 A1 10/2014

*Primary Examiner* — John E Breene
*Assistant Examiner* — Jeffrey C Morgan
(74) *Attorney, Agent, or Firm* — Werschulz Patent Law, LLC; Patricia P. Werschulz, Esq.

(57) ABSTRACT

An apparatus, a system and a method for monitoring and alerting a user caring for a patient when a change in body temperature requires immediate attention. The apparatus is a bracelet worn by the user. The system includes the bracelet in wireless communication with a temperature sensing device placed on the patient. The bracelet has a body temperature display an audible alarm that sounds and a vibration that occurs when the temperature exceeds a setpoint, and a plurality of lights, each with a unique setpoint, a light activated when the temperature exceeds the setpoint and a glowing band. The user attaches the temperature sensing device to the patient and dons the bracelet. The user can then sleep, selectively observing the display and lights upon waking with confidence that the system is monitoring the patient's temperature and selectively alerting the user when a change in body temperature requires immediate attention.

9 Claims, 12 Drawing Sheets

(56) References Cited

U.S. PATENT DOCUMENTS

| | | | |
|---|---|---|---|
| 2008/0211387 A1* | 9/2008 | Bechtel | H05B 33/145 |
| | | | 313/503 |
| 2008/0262781 A1 | 10/2008 | Valdes | |
| 2009/0221888 A1 | 9/2009 | Wijesiriwardana | |
| 2011/0137141 A1 | 6/2011 | Razoumov et al. | |
| 2011/0158284 A1 | 6/2011 | Goto | |
| 2011/0193704 A1 | 8/2011 | Harper et al. | |
| 2011/0298613 A1 | 12/2011 | Ben Ayed | |
| 2011/0320130 A1 | 12/2011 | Valdes et al. | |
| 2012/0063487 A1 | 3/2012 | Albrecht | |
| 2012/0324945 A1* | 12/2012 | Koeppel | A44C 5/0015 |
| | | | 63/1.13 |
| 2013/0154826 A1* | 6/2013 | Ratajczyk | G08B 7/06 |
| | | | 340/539.11 |
| 2013/0218022 A1 | 8/2013 | Larsen et al. | |
| 2014/0298859 A1 | 10/2014 | Balboni | |

* cited by examiner

FEVER ALERT SYSTEM

CROSS-REFERENCE TO RELATED APPLICATIONS

This application is a nonprovisional continuation-in-part utility application and claims priority thereof to the nonprovisional utility patent application, Ser. No. 14/243,422, filed in the United States Patent Office on Apr. 2, 2014, which claims priority thereof to the provisional patent application, Ser. No. 61/809,509 filed in the United States Patent Office on Apr. 8, 2013, which is expressly incorporated herein by reference in its entirety

TECHNICAL FIELD

The present disclosure relates generally to a fever alert system. More particularly, the present disclosure relates to a wearable apparatus, a remote fever alert system and method of using same.

BACKGROUND

Infants and young children often spike high fevers when ill. These high fevers often are accompanied by febrile seizures and other complications. High fevers also can indicate a serious illness such as encephalitis and meningitis.

Modern medical thinking is that a sustained moderately elevated temperature that by itself does not cause discomfort, actually helps the body fight infection. However, a spiking fever, that is a rapid rise in body temperature or a sustained high temperature is dangerous, requiring immediate attention as well as extremely uncomfortable for the patient.

Febrile seizures run in families. When a child has a history of febrile seizures or there is a family history of febrile seizures, parents and caregivers are in for sleepless nights when the child is sick, monitoring the child and staying close by.

Caregivers who provide care for the incapacitated, such as the elderly or those who cannot communicate, must also stay close by when the patient becomes ill with an accompanying fever While some temperature monitors may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a method of monitoring a sick patient, especially a sick child for a change in body temperature that requires immediate attention. Accordingly, an aspect of an example embodiment in the present disclosure provides a method of remotely monitoring the body temperature of a sick patient through a wireless sensing device coupled to an apparatus with an alarm.

Another aspect of an example embodiment in the present disclosure is to provide an apparatus that allows a caregiver to remotely maintain vigilance over a sick child. Accordingly, the present disclosure provides a bracelet in wireless communication with a body temperature sensing device, the bracelet showing the body temperature in a display and through a plurality of lights each having a unique temperature setpoint.

A further aspect of an example embodiment in the present disclosure is to provide an apparatus the allows a caregiver to sleep while maintaining vigilance over a sick child. Accordingly, the present disclosure provides a bracelet selectively worn while sleeping, the bracelet in wireless communication with a body temperature sensing device, the bracelet providing an alarm and a plurality of vibrations when a change in body temperature requires immediate attention.

Yet another aspect of an example embodiment in the present disclosure is to provide an apparatus that allows a caregiver to sleep while maintaining vigilance over a sick child. Accordingly, the present disclosure provides a bracelet selectively worn while sleeping, the bracelet in wireless communication with a body temperature sensing device, the bracelet glowing when a change in body temperature requires immediate attention.

Yet a further aspect of an example embodiment in the present disclosure is to provide an apparatus that allows a caregiver to sleep comfortably while maintaining vigilance over a sick child. Accordingly, the present disclosure provides a bracelet comprising a soft silicone band and a cloth liner selectively worn while sleeping, the bracelet in wireless communication with a body temperature sensing device.

The present disclosure describes an apparatus, a system and a method for monitoring and alerting a user caring for a patient when a change in body temperature requires immediate attention. The apparatus is a bracelet worn by the user. The system includes the bracelet in wireless communication with a temperature sensing device placed on the patient. The bracelet has a display operative for displaying the body temperature, an audible alarm that sounds and a vibrator that vibrates when the temperature exceeds a setpoint, and a plurality of lights, each with a unique setpoint, a light activated when the temperature exceeds the setpoint. The user attaches the temperature sensing device to the patient such as a young child, and dons the bracelet. The user can then sleep, selectively observing the display and lights upon waking with confidence that the system is monitoring the patient's temperature and selectively alerting the user when a change in body temperature requires immediate attention.

The present disclosure addresses at least one of the foregoing disadvantages. However, it is contemplated that the present disclosure may prove useful in addressing other problems and deficiencies in many technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

In the drawings, like elements are depicted by like reference numerals. The drawings are briefly described as follows.

DETAILED DESCRIPTION OF THE PREFERRED EMBODIMENTS

Figure 3:
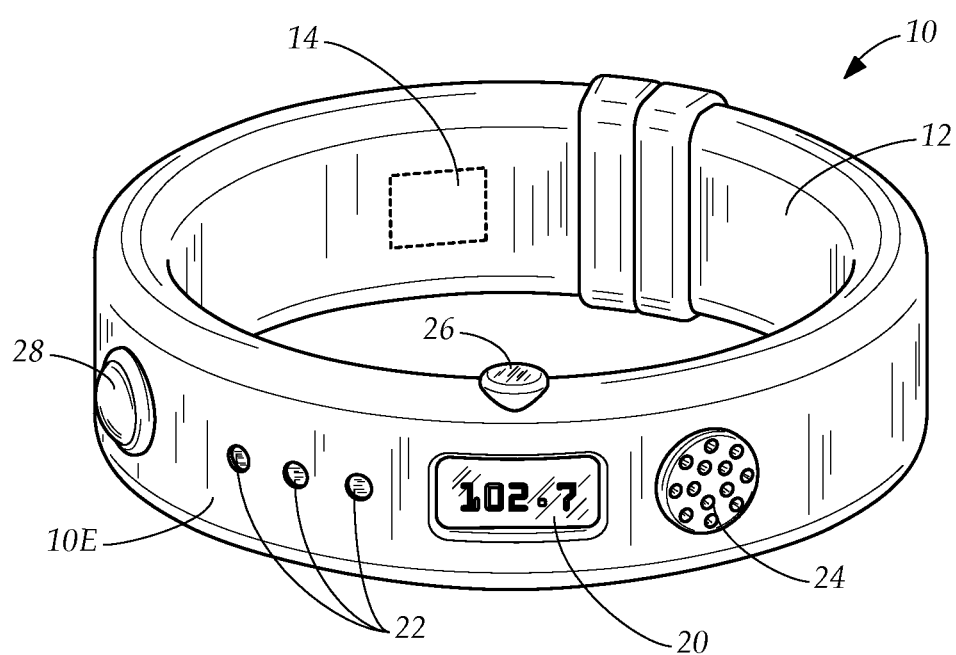
FIG. 3 is a perspective view of an example embodiment of a bracelet operative for monitoring body temperature of a patient and alerting a user of a change that requires immediate attention.

FIG. 3 illustrates an apparatus in a system for monitoring and alerting a user caring for a patient when a change in the patient's body temperature requires immediate attention. The apparatus is a bracelet 10 worn by the user. The user wears the bracelet 10, allowing the user is not be present with the patient, the user still continuously vigilant and capable of observing any changes in the patient's body temperature that indicate the patient requires immediate attention.

The bracelet 10 is comfortably worn by the user, allowing the user to sleep in a separate room from the patient and carry on activities of daily living in the vicinity of the patient. The system allows the user to remotely observe the temperature of the patient without disturbing the patient. As a non-limiting example, a parent confidently sleeps in a separate room when the child is ill, knowing that the bracelet 10 sends an alert if the child's temperature exceeds a setpoint or rapidly rises, the alert prompting the parent to immediately attend and observe firsthand, monitoring the child for seizures and other serious complications. The parent can observe the child's temperature through the bracelet 10 without entering the child's room and disturbing the child.

It is understood that this discussion often refers to a parent and a child to illustrate the utility of the disclosed embodiments, but that this is not a limitation and the disclosure is applicable to any caretaker and patient.

In one embodiment, the bracelet 10 has an internal transceiver 14 operative for wirelessly receiving a signal representing a temperature from a body temperature sensing device. The body temperature sensing device is described hereinbelow. The signal communicates the temperature detected by the sensing device to the transceiver 14 in the bracelet 10 when the device in place on a patient.

The bracelet 10 has an alarm with a speaker 24 in communication with the transceiver 14. The alarm is associated with a unique setpoint, the alarm sounding when the temperature is greater than the unique setpoint, the sounding of the alarm indicating that the patient has an elevated body temperature requiring immediate attention.

In a further embodiment, the bracelet 10 has an exterior with an interior surface 12 and an outer surface 10E. On the outer surface 10E is a display 20 in communication with the transceiver 14. The display 20 is operative for displaying the temperature detected by the temperature sensing device.

In another embodiment, the bracelet 10 has a plurality of lights 22 on the outer surface 10E. The lights 22 are in communication with the transceiver 14.

Each light 22 is associated with a unique setpoint, each light selectively shining when the temperature is greater than its unique setpoint operative for communicating the body temperature. In one embodiment, the lights are different colors. As a non-limiting example, a green light 22 has a setpoint of "normal" or non-febrile temperature. "Normal temperature" is defined by the placement of the temperature sensing device, placement in the ear having a different "normal" temperature than placement in the axilla. A yellow light 22 has a set point of a slightly elevated temperature and a red light 22 has a set point of an elevated temperature that requires attention as further non-limiting example embodiments.

In a further example embodiment, as a further non-limiting demonstration, a yellow light 22 has a setpoint of a slightly elevated temperature, an orange light 22 has a set point of slightly more elevated temperature and a red light 22 has set point of an elevated temperature that requires immediate attention. As it is understood by those of ordinary skill, the colors, setpoints and exact number of lights are not limitations and can vary within the inventive concept.

In one embodiment, the bracelet 10 has an internal controller inside, the controller coupled to the transceiver 14; the controller is not visible in the drawing. The controller is operative for wirelessly receiving the signal from the body temperature sensing device and storing a plurality of setpoints and a plurality of body temperatures.

In one example embodiment, the bracelet 10 includes a soft silicone strap, preferable for wearing during the day, although when the silicone strap is worn is not a limitation. In a further example embodiment, the bracelet 10 includes a cloth strap with a hook and loop closure operative for easy size adjustment, the cloth strap preferable for wearing when sleeping, but when the cloth strap is worn is not a limitation.

The controller is in communication with the alarm 24, the alarm associated with a unique setpoint in the controller, the controller selectively sounding the alarm, providing an audible alert when the temperature is greater than the unique setpoint, the sounding of the alarm alerting the user, indicating that the patient has a body temperature requiring immediate attention.

In one example embodiment, the alarm sounds coordinate with the setpoints of the lights 22. In a further example embodiment, a different setpoints, the frequency of the alarm varies, producing different pitches, the higher the frequency, the higher the temperature. In yet another example embodiment, the frequency of the sounding of the alarm increase with the increasing temperature. As a non-limiting example, when the yellow light 22 illuminates indicating a slightly elevated temperature, the alarm sounds twelve times a minute. When the orange light 22 illuminates, the alarm sounds every second and when the red light 22 illuminates, the alarm is constant. Alternatively, the alarm is a rapid staccato.

The controller in the bracelet 10 monitors change in temperature at preset intervals, calculates a derivative indicating a rate of change and sounding the alarm when the derivative exceeds a preset limit indicating a rapid spike in temperature requiring immediate attention.

In a further embodiment, the controller is in communication with the display 20, the controller directing the display 20 to show the temperature detected by the temperature sensing device. The controller is in communication with the lights 22, each light 22 associated with a unique setpoint in the controller, the controller selectively activating each light 22 when the detected temperature is greater than its unique setpoint.

The bracelet 10 has a switch 26 for selectively illuminating the display 20. The display 20 is not illuminated without selecting the switch 26 so that the user wearing the bracelet 10 when sleeping is not disturbed by the illuminating display 20, nor is any other person in the vicinity of the parent, who may also be trying to sleep.

The bracelet 10 has a soft key button 28, the soft key button 28 operative for selecting the unique setpoints through the display 20. In another embodiment, the soft key button 28 is operative for resetting the controller, changing the unique setpoints in the controller through the display 20. The soft key button 28 selectively deactivates all alerts.

In one embodiment, the bracelet 10 has an internal vibrator, the vibrator associated with a unique setpoint, the vibrator vibrating when the temperature is greater than the unique setpoint, the vibrator vibrating the bracelet 10 operative for alerting a user.

Figure 4:
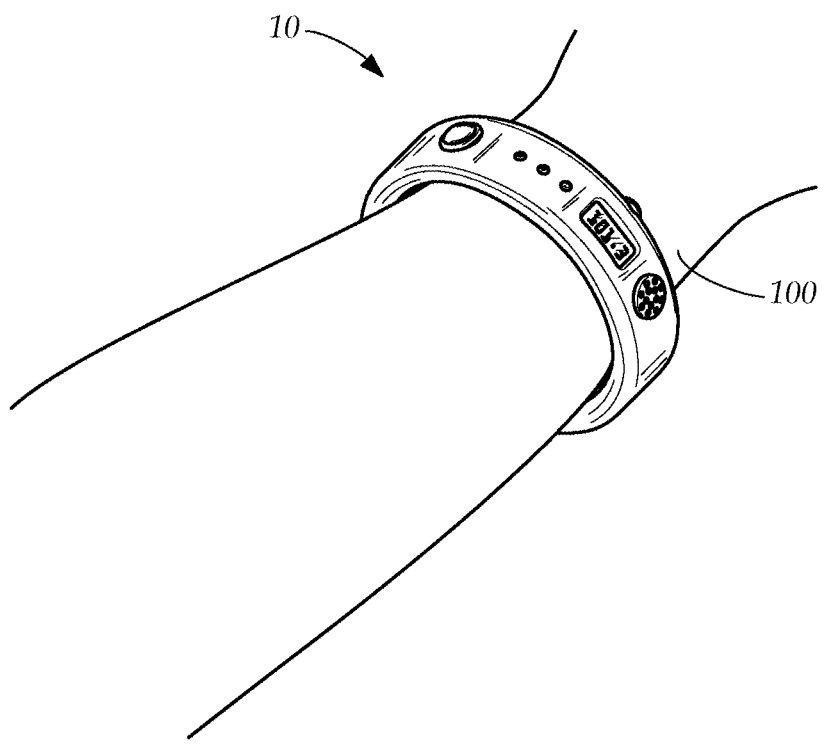
FIG. 4 is a perspective view of the bracelet worn on a wrist of the user.

In a further embodiment, the bracelet 10 has an interior conductive surface 12, the conductive surface in direct contact with a user's skin when the bracelet 10 is worn. The conductive surface 12 is coupled to the controller, the controller selectively transmitting an electric current to the conductive surface when the temperature is greater than the unique setpoint in the controller, the conductive surface mildly shocking the skin operative for alerting the user. FIG. 4 shows the bracelet 10 on a wrist 100 of the user in contact with a user's skin. It is understood that the present disclosure discusses a plurality of sensory signals indicating elevated temperatures that includes visual, aural and contact signals such as vibration and mild shock and that those of ordinary skill understand that other forms of sensory signals are possible within the inventive concept.

Figure 3A:
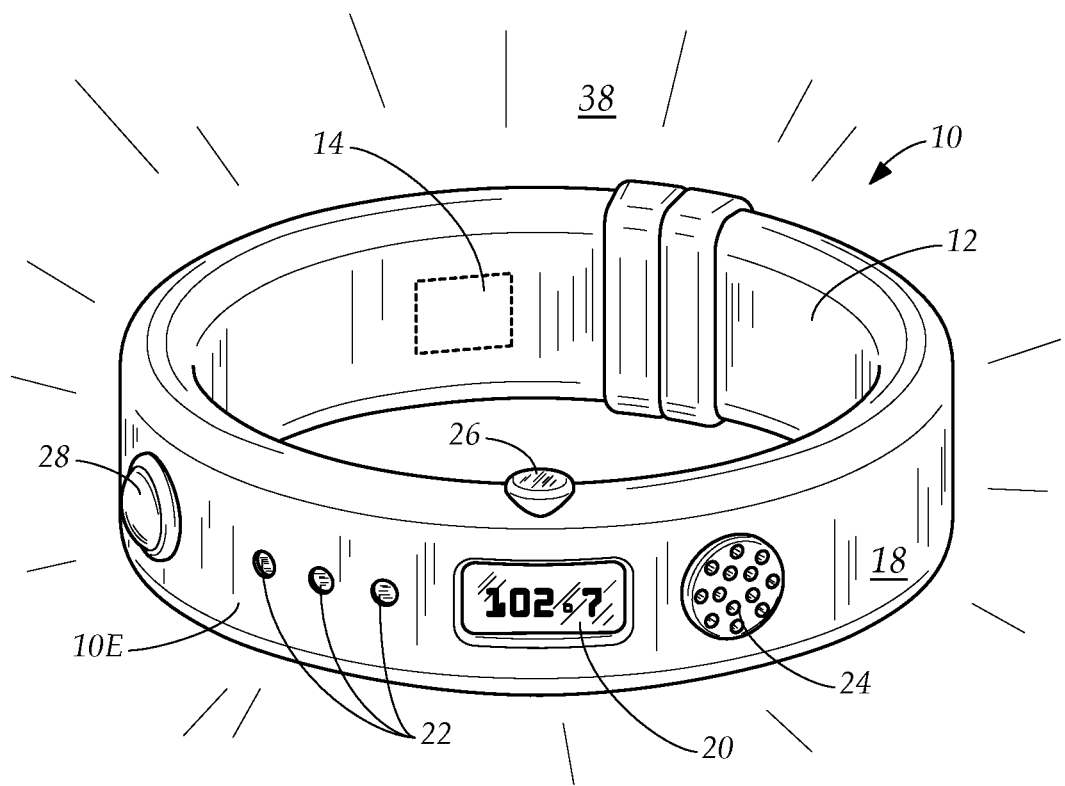
FIG. 3A, similar to FIG. 3, is a perspective view of another example embodiment of the bracelet.

FIG. 3A shows another example embodiment of the bracelet 10. The bracelet is a soft silicone band 18 that accommodates the controller in communication with the transceiver 14. The soft silicone band 18 has an internal glowing mechanism in communication with the controller that is in communication with the internal transceiver 14. The internal glowing mechanism produces an external glow 38 on the silicone band 18 when activated. Similar to the alarm 24 as described hereinabove, the controller selectively activates the internal glowing mechanism within the silicone band when the temperature detected by the body temperature sensing device is greater than its unique setpoint.

As described hereinabove with regard to the alarm 24, the controller 14 selectively activates the glowing mechanism within the soft silicone band 18 when a change in the body temperature from a first body temperature setpoint to a second body temperature setpoint is rapid such the derivative of the change exceeds a preset limit.

The soft silicone band 18 comprises luminescent material that glows when activated by the controller. This material may be compounded with the silicone, captured within the polymeric silicone or may be discrete particles incorporated in silicone band. The luminescent material may be electroluminescent compounds or tiny LED (light-emitting diodes) embedded in the band. In one example embodiment, the luminescent material glows different colors indicating that the body temperature has reached a unique setpoint as described hereinabove with reference to the lights 22 on the outer surface 10E.

In one example embodiment, the bracelet 10 further comprises the lights 22 on the outer surface 10E, as described hereinabove. Each light 22 is associated with the unique setpoint as described hereinabove, each light selectively shining when the temperature is greater than its unique setpoint operative for communicating the body temperature. In one embodiment, the lights are different colors.

The bracelet 10 may further comprise the display 20 and the internal vibrator as described hereinabove.

Figure 3B:
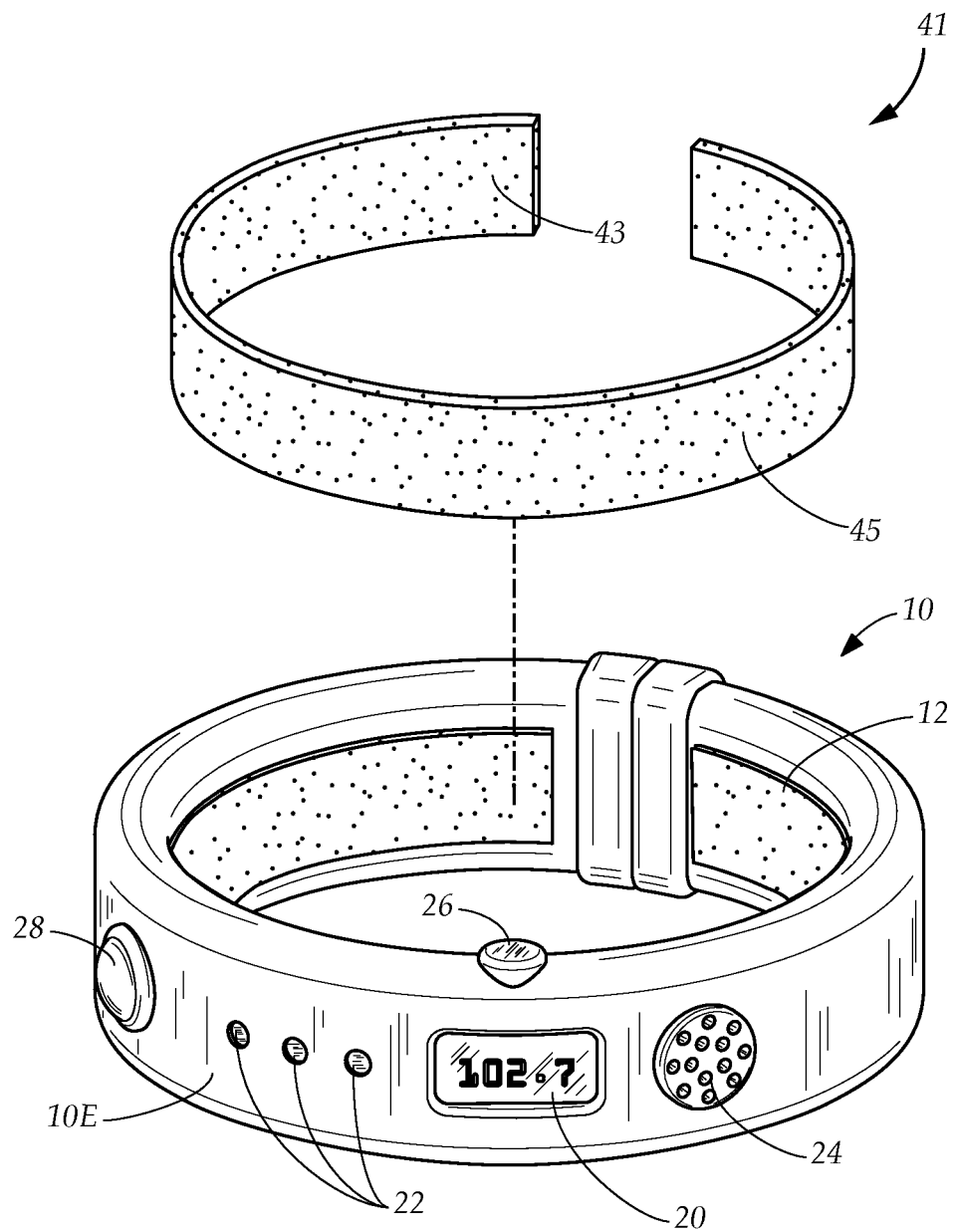
FIG. 3B, similar to FIG. 3 is a perspective view of a further example embodiment of the bracelet.

FIG. 3B demonstrates a further example embodiment of the bracelet 10. The bracelet 10 has an inner cloth lining 41 worn for selectively covering the inner surface 12 of the soft silicone band 18. The cloth lining 41 has an inner surface 43 that is moisture wicking fabric and an outer surface 45 that is slightly tacky operative for clinging to the silicone band 18.

The bracelet 10 has the display 20, the lights 22 on the outer surface 10E and the alarm 24 as explained herein above. Each light 22 is associated with the unique setpoint as described hereinabove, each light selectively shining when the temperature is greater than its unique setpoint operative for communicating the body temperature. In one embodiment, the lights are different colors.

Figure 3C:
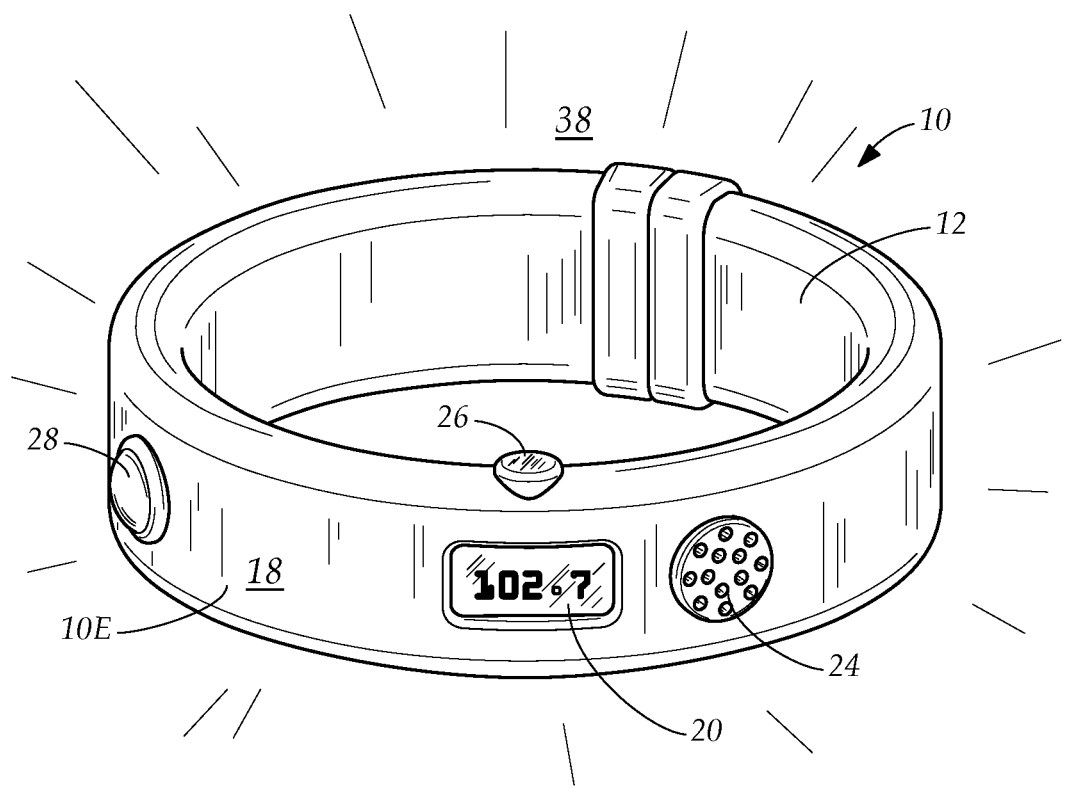
FIG. 3C, similar to FIG. 3 is a perspective view of yet another example embodiment of the bracelet.

FIG. 3C shows yet another example embodiment of the bracelet 10. The silicone band 18 has the internal glowing mechanism in communication with the controller. The internal glowing mechanism produces the external glow 38 on the silicone band 18 when activated. In this example embodiment as drawn, the display 20, alarm 24 and vibrator are present and function as described hereinabove. As those of ordinary skill in the art understand, FIGS. 3-3C demonstrate that the external glowing 38 produced by the internal glowing mechanism, the cloth lining 41, the display 20, lights 22, alarm 24 and vibrator need not all be present and that various combinations of these features may be present in the various example embodiments.

Figure 1:
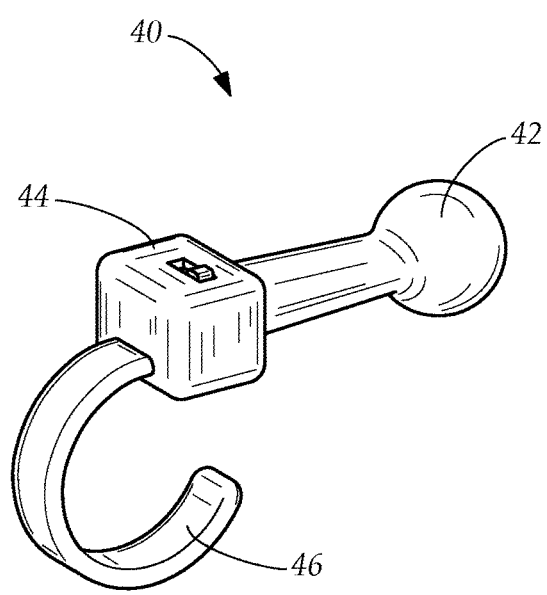
FIG. 1 is perspective view of an example embodiment of a body temperature monitoring device for placing in an ear of a patient.
Figure 2:
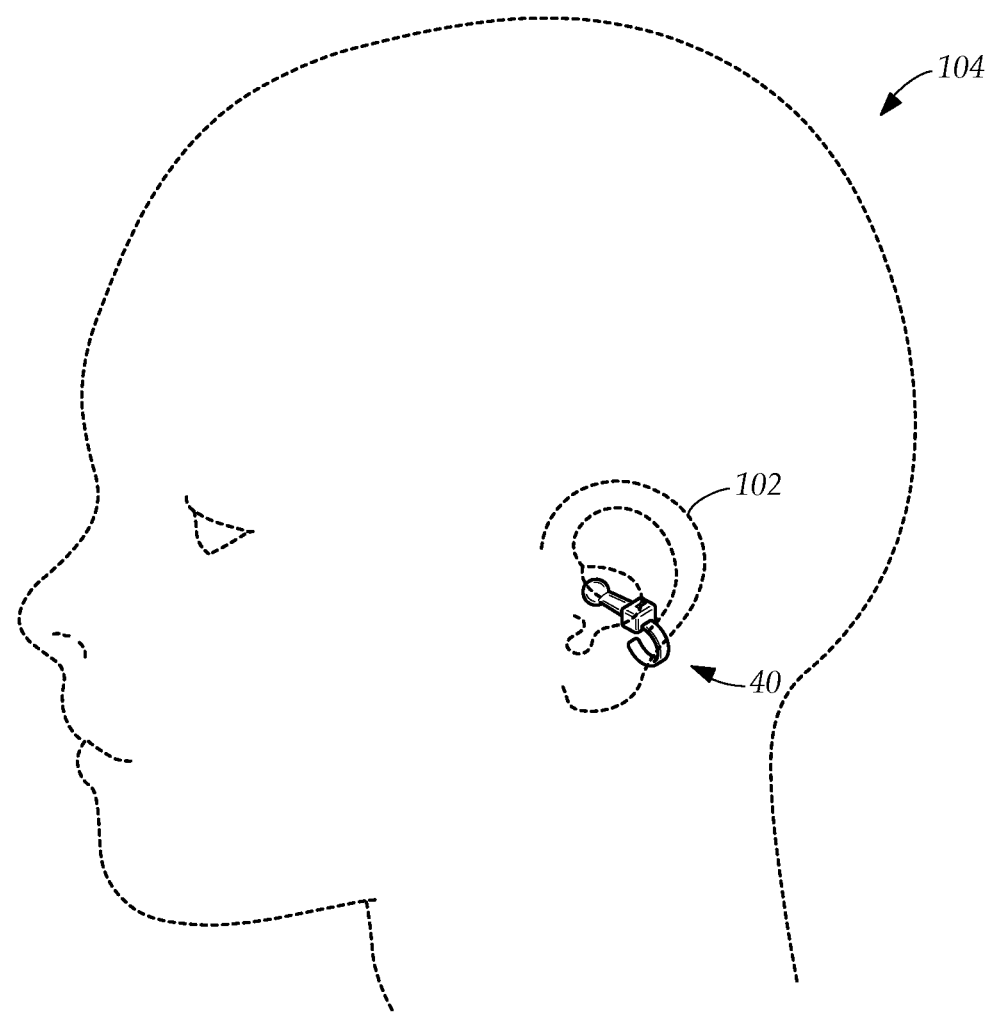
FIG. 2 is perspective view of the body temperature monitoring device in place on the ear of a patient, the patient shown in outline.

FIG. 1 demonstrates an example embodiment of a body temperature sensing device 40 in the system. The device has a probe 42 that inserts into an outer ear canal of the patient and measures the body temperature. In the drawing, the probe is bulbous in shape as a non-limiting example and it is understood the probe is not limited to one particular shape, but can also be, as a non-limiting example, conical or frustoconical. The device 40 has a transmitter 44 and an auricle clip 46 for attaching 40 the device to an outer ear auricle. FIG. 2 shows the device 40 attaching to the auricle 102 of the patient 104.

Figure 9A:
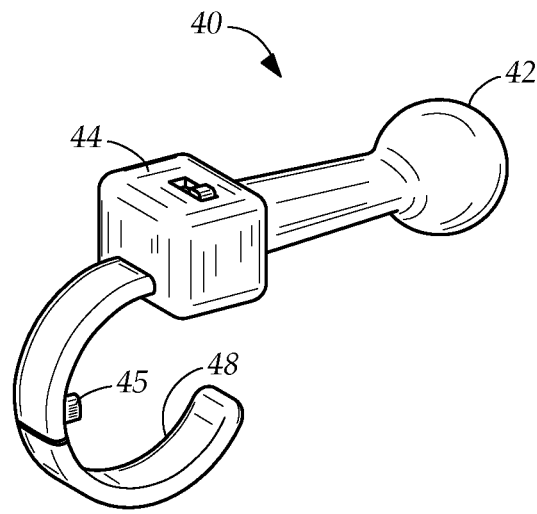
FIG. 9A is a perspective view of another example embodiment of a body temperature monitoring device for locking on an ear of a patient in a locked position.
Figure 9B:
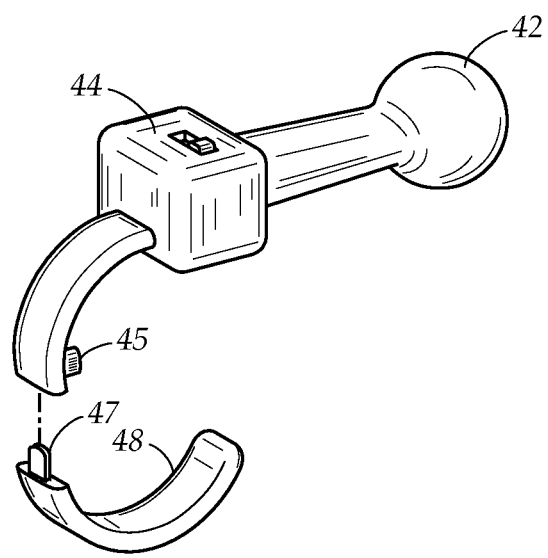
FIG. 9B, similar to FIG. 9A, is a perspective view of another example embodiment of a body temperature monitoring device for locking on an ear of a patient in an open position.

FIG. 9A and FIG. 9B show another example of a locking auricle clip 48. The clip 48 is a two-part locking clip that includes a cam 47 and a child-resistant release 45 forming a child-resistant lock on the clip 48, maintaining the body temperature sensing device in place on the outer ear canal when a sick child or delirious adult patient tries to remove it. To release the clip, the user pushes the child-resistant release, releasing the cam 47, the locking auricle clip 48 opening for easy removal.

It is understood by those of ordinary skill that other example embodiments of the temperature sensing device, such as, for example, but not limited to an axillary sensor, a rectal sensor and an oral sensor, are possible within the inventive concept and such example embodiments are not to be construed as limitations.

Figure 6:
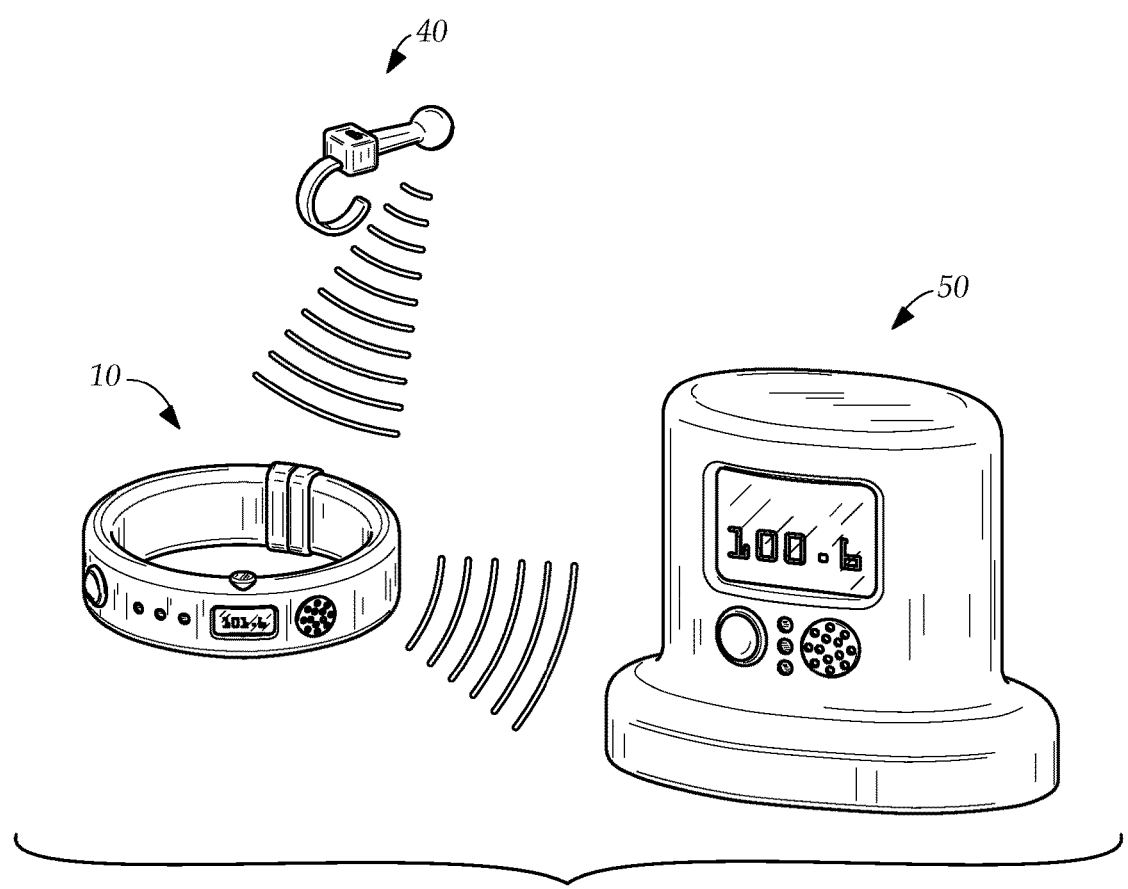
FIG. 6 is a perspective view of a system operative for monitoring body temperature of the patient.

FIG. 6 shows the system for monitoring and alerting the user caring for the patient when the change in body temperature requires immediate attention.

In this example embodiment, the body temperature sensing device 40 is an aural sensor operative for wirelessly transmitting a signal communicating a body temperature when in place on the patient's auricle.

The system includes the bracelet 10 worn by a user described hereinabove, the bracelet 10 operative for wirelessly receiving the signal from the body temperature sensing device 40. The bracelet 10 is operative for alerting the user, indicating that the patient has a body temperature requiring immediate attention.

In a further example embodiment, the system further comprises a monitor 50 having a transceiver 14 operative for wirelessly receiving a signal from the controller in the bracelet 10.

Figure 5:
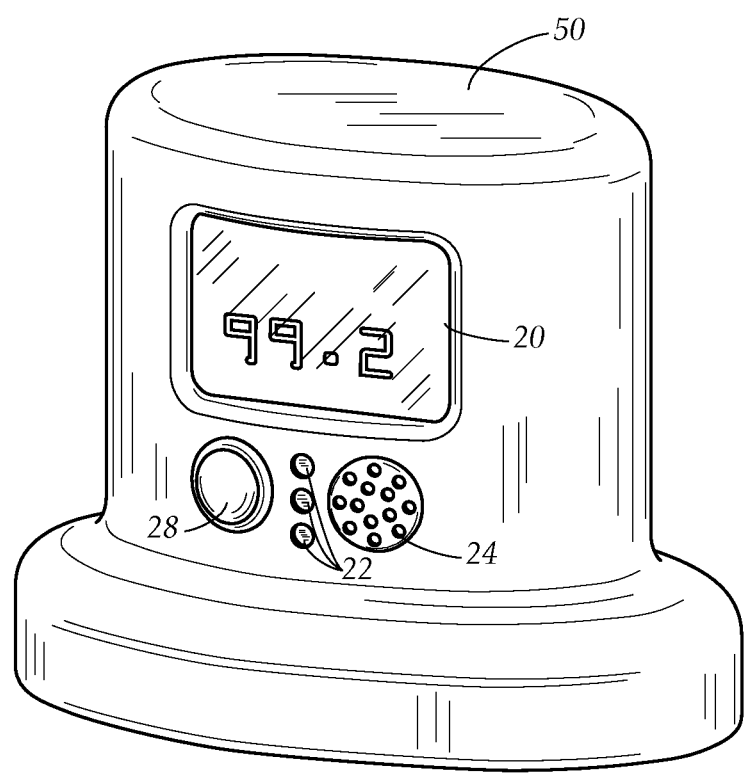
FIG. 5 is a perspective view of an example embodiment of a monitor operative for observing body temperature of the patient and alerting the user of a change that requires attention.

As shown in FIG. 5 and FIG. 6, the monitor 50 has a display 20 in communication with the bracelet 10 through the bracelet controller, the bracelet controller directing the display 20 to show the temperature detected by the temperature sensing device 40.

The monitor 50 further has lights 22 in communication with the bracelet controller, each light associated with a unique setpoint in the controller. The lights 22 replicate the lights 22 on the bracelet 10, the lights 22 operating as explained hereinabove.

The monitor 50 further has the alarm 24 in communication with the bracelet controller, the alarm replicating the alarm on the bracelet 10, the alarm sounding, alerting the user, indicating that the patient has a body temperature requiring immediate attention.

Figure 7:
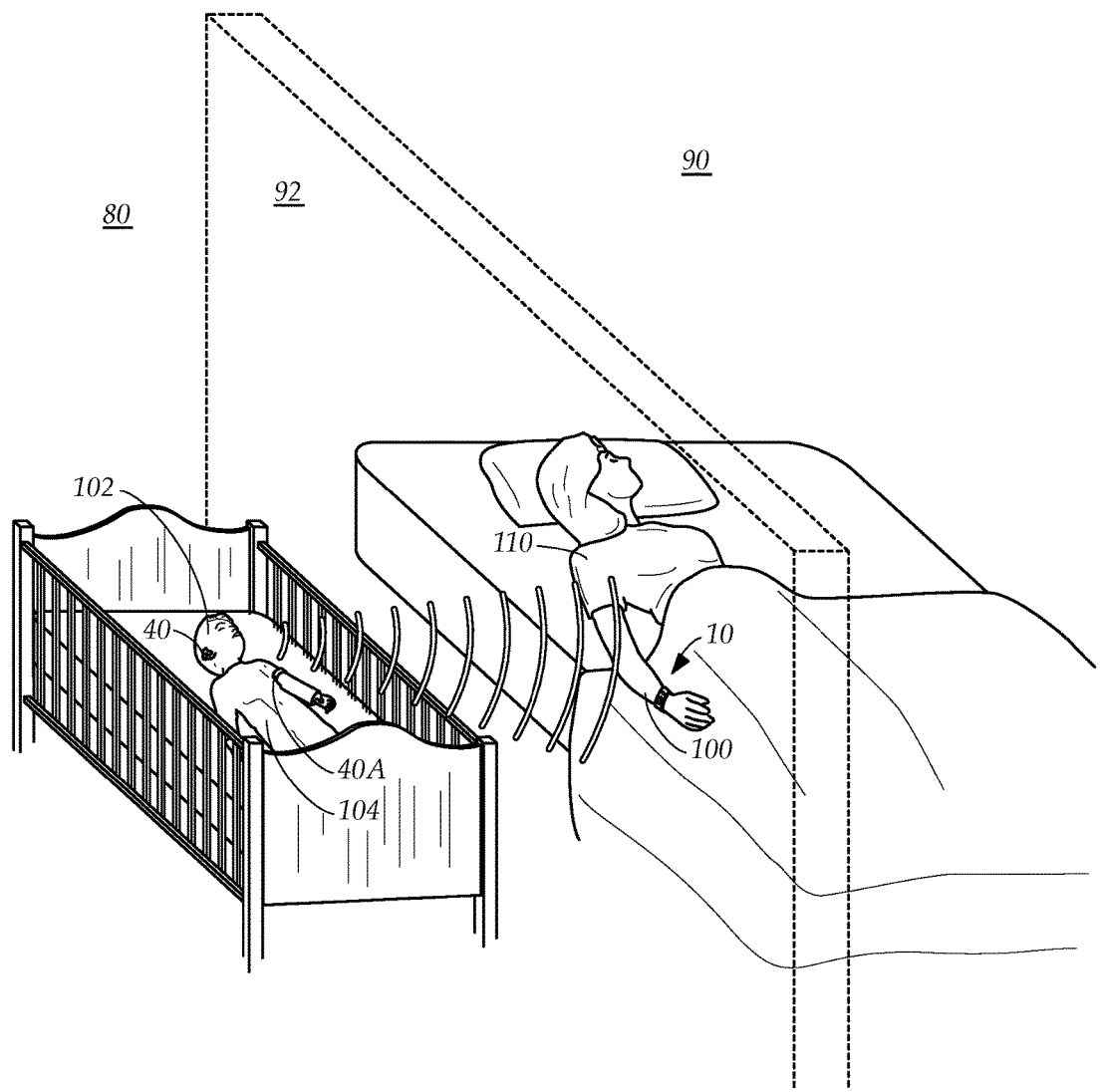
FIG. 7 is a perspective view of the system in use, the user wearing the bracelet and the patient wearing the temperature sensing device.

FIG. 7 is an illustration of an example embodiment of the system in use. The user 110, who is the caregiver sleeps in a first room 90, the patient 104 sleeping in a second room 80 with a wall 92 separating the rooms 80, 90. It is understood that more than one wall or no wall can separate the user and the patient, the drawing presented as a non-limiting example. The user 110 is wearing the bracelet 10 on the wrist 100.

The patient 104 sleeps with the temperature sensing device 40 in place. In one example embodiment, the device 40 is place in the ear on the patient's head 102. In a further example embodiment, the temperature sensing device 40A is on an arm band placed on a patient's upper arm, the device having a probe in place engaging an axilla. It is understood that the system requires only one device and the two examples embodiments in the drawing are for illustrative purposes, showing alternative devices.

FIG. 7 further demonstrates a method for alerting the user 110 caring for the patient 104 when a change in body temperature requires immediate attention.

The method comprises the user 110 attaching the body temperature sensing device 40, 40A to the patient 104, the device 40 operative for wirelessly communicating the body temperature of the patient 104.

The user 110 dons the bracelet 10, the bracelet having a controller operative for wirelessly receiving the signal from the device 40.

The user 110 observes the body temperature of the patient by looking at the display 20 and the lights on the bracelet 10, the operation of which is explained hereinabove and illustrated in FIG. 3. The user 110 determines which lights 22 are activated, the activated lights 22 indicating the temperature is greater than the setpoint of the activated lights 22.

The user 110 selectively receives the alert indicating that the patient 104 has body temperature requiring immediate attention by hearing the sounding of the alarm 24 on the bracelet 10 alerting the user. In a further example embodiment, the user 110 receives a shock. In another example embodiment, the user 110 feels vibrations.

As described hereinabove, the bracelet 10 further comprises a soft key button 28 operative for changing the unique setpoints in the controller through the display 20 and the method further comprises the user 110 setting the setpoints in the controller with the soft key button 28.

As further described hereinabove, the bracelet 10 has a display switch 26 for selectively illuminating the display 20 and the method further comprises the user 110 selectively illuminating the display 20 with the switch 26.

Referring to FIG. 3, an example embodiment of a method for providing the bracelet 10 comprises, coupling a transceiver 14 to the interior surface 12 of the bracelet 10. In another example embodiment, the controller is coupled to the interior surface 12 of the bracelet 10.

The method further comprises coupling the alarm to the bracelet, the alarm having a speaker 24 on the exterior outer surface 10E of the bracelet, the alarm in communication with the transceiver 14. In a further example embodiment, the alarm is in communication with the controller 14.

In one example embodiment, the method further comprises coupling the lights 22 to the bracelet 10 on the exterior outer surface 10E, the lights 22 in communication with the transceiver 14. In a further example embodiment, the lights 22 are in communication with the controller.

Figure 8:
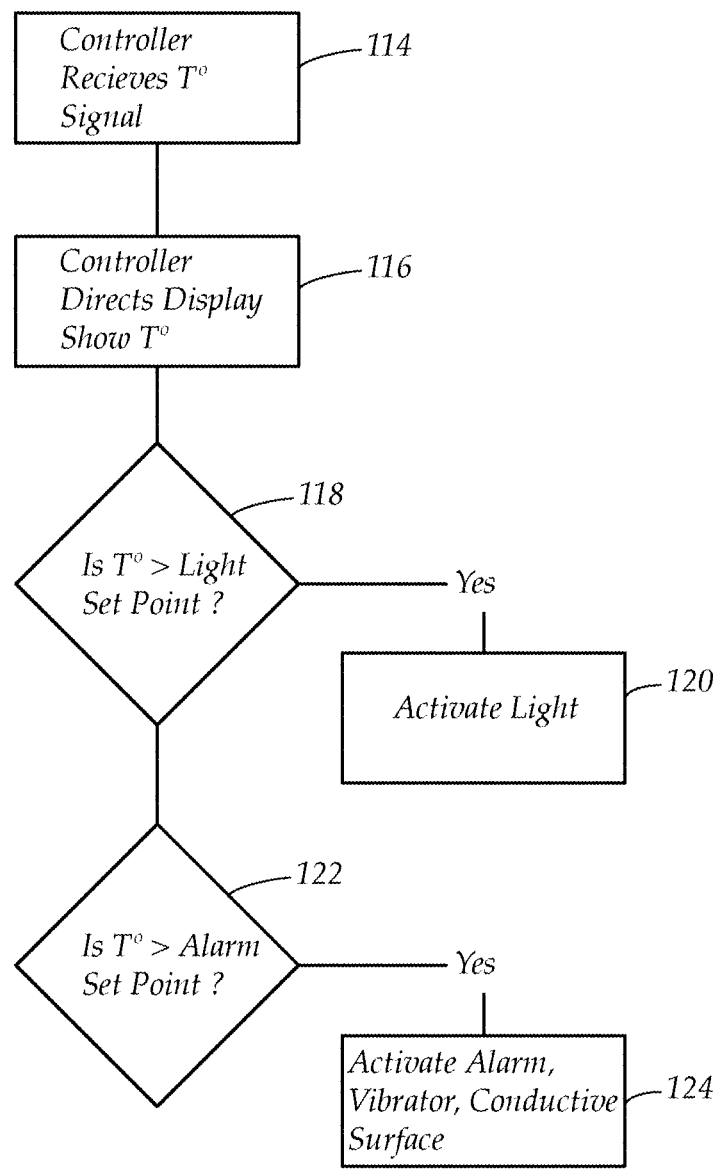
FIG. 8 is a block diagram showing the steps of a method in the system. The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

In a further example embodiment, the method further comprises coupling the display 20 to the outer surface 10E of the bracelet, the display 20 in communication with the transceiver 14. In a further example embodiment, the display 20 is in communication with the controller Referring to FIG. 8, an example embodiment of a method of bracelet operation, bracelet having the controller, is described. The controller receives a body temperature signal from the temperature sensing device 114.

In one embodiment, the controller directs the display to show the body temperature 116. In a further embodiment, the controller determines if the temperature is above the setpoint of each light 118. If the temperature is above the setpoint of the light, the controller activates the light 120.

The controller determines if the temperature s above the setpoint of the alarm 122. If the temperature is above the setpoint of the alarm, in one embodiment, the controller sounds the alarm, in another embodiment, the activates the vibrator, in a further embodiment, sends a shock to the conductive surface 124.

FIG. 6 demonstrates a method for facilitating a system for alerting the user when a change in the patient's body temperature requires immediate attention. The method comprises providing the body temperature sensing device 40 operative for wirelessly transmitting a signal communicating a body temperature of a patient and providing the bracelet 10 operative for wirelessly receiving the signal from the body temperature sensing device, the bracelet providing an alert when the temperature is greater than the unique setpoint, as described hereinabove.

In a further embodiment, the method further comprises providing the monitor 50 in wireless communication with the bracelet 10, the monitor 50 replicating the alarm sounded by the bracelet 10.

The disclosed embodiments may individually and/or collectively be components of a larger system, wherein other procedures may take precedence over or otherwise modify their application. Also, a number of steps may be required before, after, and/or concurrently with the following embodiments.

As will be appreciated by one skilled in the art, aspects of the present disclosure may be embodied as a system, method or software application product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "system." Furthermore, aspects of the present disclosure may take the form of a software application product embodied in one or more readable media having readable program code embodied thereon.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a wearable apparatus such as a bracelet, a remote fever alert system and method of using same. The disclosure is illustrated by example in the drawing figures, and throughout the written description. It should be understood that numerous variations are possible, while adhering to the inventive concept. Such variations are contemplated as being a part of the present disclosure.

What is claimed is:

1. A bracelet for monitoring and alerting a caregiver when a patient has a change in body temperature, comprising:
a controller operative for wirelessly receiving a signal representing a temperature from a body temperature sensing device on a patient, the controller storing a plurality of body temperature setpoints; and
a soft silicone band accommodating the controller, the soft silicone band having an internal glowing mechanism in communication with the controller, the internal glowing mechanism producing an external glow on the entire soft silicone band when activated, the entire soft silicone band comprising luminescent material that glows when activated by the controller, the controller selectively activating the internal glowing mechanism within the silicone band when a temperature detected by the body temperature sensing device is greater than its unique setpoint and the controller selectively activating the glowing mechanism within the soft silicone band when a change in the body temperature from a first body temperature setpoint to a second body temperature setpoint is rapid such the derivative of the change exceeds a preset limit.

2. The bracelet as described in claim 1, wherein the soft silicone band further comprises an electroluminescent compound that glows when activated by the controller, producing an external glow on the entire soft silicone band.

3. The bracelet as described in claim 1, wherein the soft silicone band further comprises a plurality of internal LED lights inside the soft silicone band that glow when activated by the controller, producing an external glow on the entire soft silicone band.

4. The bracelet as described in claim 1, further comprising a display in communication with the controller, the controller directing the display to show the temperature detected by the body temperature sensing device.

5. The bracelet as described in claim 1, further comprising an internal vibrator in communication with the controller, the vibrator associated with a unique setpoint in the controller, the controller selectively activating the vibrator when the temperature detected by the body temperature sensing device is greater than the unique setpoint.

6. The bracelet as described in claim 1, further comprising an alarm in communication with the controller, the alarm associated with a unique setpoint in the controller, the controller selectively sounding the alarm when the temperature detected by the body temperature sensing device is greater than the unique setpoint.

7. A bracelet for monitoring and alerting a caregiver when a patient has a change in body temperature, comprising:
- a controller operative for wirelessly receiving a signal representing a temperature from a body temperature sensing device on a patient, the controller storing a plurality of body temperature setpoints;
- a soft silicone band accommodating the controller, the soft silicone band having an internal glowing mechanism in communication with the controller, the internal glowing mechanism producing an external glow on the entire soft silicone band when activated, the entire soft silicone band further comprising luminescent material that glows when activated by the controller, the controller selectively activating the internal glowing mechanism within the silicone band when the temperature detected by the body temperature sensing device is greater than its unique setpoint and the controller selectively activating the glowing mechanism within the soft silicone band when a change in the body temperature from a first body temperature setpoint to a second body temperature setpoint is rapid such the derivative of the change exceeds a preset limit;
- a display on the outer surface of the soft silicone band, the display in communication with the controller, the controller directing the display to show the body temperature detected by the body temperature sensing device;
- a plurality of lights in communication with the controller, the lights on the outer surface of the soft silicone band, each light associated with a unique setpoint in the controller, the controller selectively activating each light when the temperature detected by the body temperature sensing device is greater than its unique setpoint;
- an alarm in communication with the controller, the alarm associated with a unique setpoint in the controller, the controller selectively sounding the alarm when the temperature detected by the body temperature sensing device is greater than the unique setpoint; setpoint and the controller selectively sounding the alarm when a change in the body temperature from a first body temperature setpoint to a second body temperature setpoint is rapid such the derivative of the change exceeds a preset limit; and
- a cloth lining worn for selectively covering the inner surface of the soft silicone band.

8. The bracelet as described in claim 7, wherein the soft silicone band further comprises an electroluminescent compound that glows when activated by the controller.

9. The bracelet as described in claim 7, wherein the soft silicone band further comprises a plurality of internal LED lights inside the soft silicone band that glow when activated by the controller.

* * * * *